United States Patent
Chwalisz et al.

(10) Patent No.: US 6,362,237 B1
(45) Date of Patent: *Mar. 26, 2002

(54) COMPOUNDS WITH PROGESTERONE-ANTAGONISTIC AND ANTIESTROGENIC ACTION TO BE USED TOGETHER FOR FEMALE CONTRACEPTION

(75) Inventors: Kristof Chwalisz; Klaus Stöckemann, both of Berlin (DE)

(73) Assignee: Schering Aktiengesellschaft, Berlin (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/578,222

(22) Filed: Dec. 26, 1995

(30) Foreign Application Priority Data

Dec. 23, 1994 (DE) .......................................... 44 474 02

(51) Int. Cl.[7] .......................... A61P 15/18; A61K 31/56
(52) U.S. Cl. ...................... 514/843; 514/170; 514/171; 514/182
(58) Field of Search ............................... 514/170, 171, 514/182, 843

(56) References Cited

U.S. PATENT DOCUMENTS 4,670,426 A * 6/1987 Zor et al. .................... 514/171
4,888,331 A   12/1989 Elger et al. ................. 514/170
5,183,814 A * 2/1993 Dukes .......................... 514/171

FOREIGN PATENT DOCUMENTS

EP              404283            * 12/1990

OTHER PUBLICATIONS

HCAPLUS abstract, AN 1991:164625, Cleve, A. et al., EP 404283 A2 (1990).*

* cited by examiner

Primary Examiner—Edward J. Webman
(74) Attorney, Agent, or Firm—Millen, White, Zelano & Branigan, P.C.

(57) ABSTRACT

This invention describes the use of at least one compound with a progesterone-antagonistic (PA) action and at least one compound with an antiestrogenic (AE) action, each in a non-ovulation-inhibiting dosage in a single dosage unit, for the production of pharmaceutical agents for female contraception.

34 Claims, 2 Drawing Sheets

RECEPTIVITY INHIBITION/GUINEA PIGS AFTER POSTCOITAL TREATMENT
Treatment: d1–d6 p.c./Administration: s.c./Autopsy: d12 p.c. (n=6/group)

COMPOUNDS WITH PROGESTERONE-ANTAGONISTIC AND ANTIESTROGENIC ACTION TO BE USED TOGETHER FOR FEMALE CONTRACEPTION

This invention relates to the use of at least one compound with progesterone-antagonistic (PA) activity and at least one compound with antiestrogenic (AE) activity, each in a non-ovulation-inhibiting dosage in a single dosage unit, for the production of pharmaceutical agents for female contraception.

The pharmaceutical agents produced according to the invention exert their contraceptive action based on receptivity inhibition, by preventing nidation of a fertilized egg cell in the mucous membrane of the uterus, without ovulation or the cycle being disrupted.

Already all over the world, the use of oral contraceptives has developed into a business factor that cannot be ignored. Especially in view of the fact that the world population is continuing to shoot upward, further development of the hitherto proven methods for birth control is absolutely necessary.

The use of competitive progesterone antagonists in female birth control both in various animal species and in humans has been discussed for some years now, as can be found in the publications listed below, in which especially the use of RU 38 486 11β-[4-dimethylamino)phenyl]-17β-hydroxy-17α-(1-propinyl)estra-4,9-dien-3-one; EP-A-0057115) has been cited in this connection:

Collins et al., Blockade of the Spontaneous Mid-Cycle Gonadotrophin Surge in Monkeys by RU 486; A Progesterone Antagonist or Agonist. J. Cli. Metab., 63: 1270–1276 (1986);

Croxatto, H. B., Salvatierra 1990 Cyclic Use of Antigestagens for Fertility Control. IIIrd International Symposium on Contraception, Heidelberg, Jun. 19–23, 1990;

Danford et al., Contraceptive Potential of RU 486 by Ovulation Inhibition. III. Preliminary Observations on Once Weekly Administration. Contraception 40: 195–200 (1989);

Kekkonen et al., Lähteoenmäki P 1990 Interference with Ovulation by Sequential Treatment with the Antiprogesterone RU 486 and Synthetic Progestin. Fertil Steril [Fertile Sterile] 53: 4747 (1990);

Puri et al., Gonadal and Pituitary Responses to Progesterone Antagonist ZK 98 299 During the Follicular Phase of the Menstrual Cycle in Bonnet Monkeys. Contraception 39(2): 227–243 (1989);

Puri et al., Contraceptive Potential of a Progesterone Antagonist ZK 98 734 {(Z)-11β-[4-(dimethylamino)phenyl]-17β-hydroxy-17α-(3-hydroxy-1-propenyl)estra-4, 9dien-3-one}: Effect on Folliculogenesis, Ovulation and Corpus Luteum Function in Bonnet Monkeys. In Moudgal et al., (eds) (1990).

The contraceptive effect of a progesterone antagonist is caused, on the one hand, by the ovulation-inhibiting action, and, on the other hand, by the direct effects on the endometrium.

In this connection, it should be mentioned that the dosage of a competitive progesterone antagonist that exerts an ovulation-inhibiting action depends very heavily on the respective competitive progesterone antagonist:

In the case of progesterone antagonists of the RU 486 type, these are little-dissociated compounds with a very strongly pronounced ovulation-inhibiting action.

Progesterone antagonists of the onapristone type are endometrium-specific (greatly dissociated) compounds that inhibit ovulation only at high dosages. Chronic treatment with such progesterone antagonists leads to retardation of the growth of the endometrium, in which case the ovarian and menstrual cycles are not disrupted. In the endometrium, this results in degeneration of endometrial glands and in compression of the stroma, so that the implantation of a fertilized egg is prevented (inhibition of receptivity).

The class of 11β-aryl- or 11β,19-arylene-substituted steroids is distinguished pharmacologically according to their strong progesterone- or glucocorticoid-antagonistic action. Thus, RU 468 can be used, on the one hand, to bring about a therapeutically-induced abortion (the human abortive dosage in combination with a prostaglandin is approximately 200–600 mg; EP-A 0 139 608), but also, on the other hand, via its antagonistic action on a glucocorticoid receptor, to treat Cushing's syndrome.

Another possible use of competitive progesterone antagonists for female birth control, the so-called "LH+2" treatment, is proposed by Swahn et al. [The Effect of RU 486 Administration During the Early Luteal Phase on Bleeding Pattern, Hormonal Parameters and Endometrium, Human Reproduction 5(4): 402–408 (1990)], by an ovulation-inhibiting RU 486 dosage unit being administered (luteal contraception) one time 2 days after the increase in the luteinizing hormone (LH) in the female menstrual cycle (this is generally on day 14, 15 or 16). Treatment with RU 486 in this portion of the menstrual cycle does not result in disruption of the cycle. At dosages above 1 mg/day, administration of RU 486 in other phases of the cycle results either in amenorrhea or in bleeding. This process has no practical importance, however, since determining the LH peak in a simple and precise manner still represents a problem.

Glasier et al. [Mefepristone (RU 486) Compared with High-Dose Estrogen and Progestogen for Emergency Postcoital Contraception, The New England J. of Med. 327: 1041–1044 (1992)] also describes the use of RU 486 for postcoital contraception (emergency postcoital contraception). The method shows a low level of side effects in addition to high effectiveness. An extension of the cycle occurred in a high percentage of women in this study. This effect can be attributed primarily to the antiovulatory action of RU 486.

In addition, WO 93/23020 describes that competitive progesterone antagonists in a dose that lies both below the abortive and ovulation-inhibiting dosage can be used for female birth control. Here, however, generally weekly or repeated and thus regular administration is necessary to achieve the desired effect.

EP-A 0 219 447 also describes what effects the daily administration of a progesterone antagonist triggers with respect to the endometrial differentiation state during the follicular phase or optionally also the luteal phase of the female cycle in a period of up to 4 days in a dosage of 10–200 mg. The changes in the endometrium that result in this connection are used with respect to the time of nidation for in vitro fertilization.

Batista et al. [Daily Administration of the Progesterone Antagonist RU 486 Prevents Implantation in the Cycling Guinea Pig. Am. J. Obstet. Gynecol. 165: 82–86 (1991)] also describes the use of RU 486 for female birth control, which in an ovulation-inhibiting dosage prevents nidation in guinea pigs by daily intake, precoitally and throughout the entire further cycle.

Kawano et al. [Effect of RU 486 on Glycogen Metabolism in Endometrium. Acta Obstetrica et Gynaecologica Japonica, 41: 1507–1511, (1989)] describes the influence of RU 486 at a dosage of 30 mg/kg of body weight on the endometrial glycogen metabolism in a rat model, so that successful egg implantation is disrupted. Administration is done, however, on day 2 or 4 of the pregnancy.

Hormonal control of implantation is species-dependent. In all mammals studied so far, the presence of ovarian progesterone is necessary for successful implantation. In the case of postcoitally ovariectomized rats and mice, which are substituted with progesterone, no implantation results, however, without the administration of estrogen (Finn C A, Porter D G [1975] Implantation of Ova [Chapter 6] and The Control of Implantation and the Decidual Reaction [Chapter 8]; In Finn C A and Porter [eds] The Uterus, Elek Science, London, pp. 57–73; 86–95). If estrogen is injected into this animal species, implantation of the blastocysts occurs immediately (delayed implantation model). These observations indicate that ovarian estrogen in the presence of progesterone induces implantation in rodents. It was already known that in guinea pigs and primates, ovarian estrogens are not essential for implantation. In the case of guinea pigs that were ovariectomized after mating, implantation takes place only after progesterone substitution (without additional estrogen treatment) (Deansley R [1972] Retarded Embryonic Development and Pregnancy Termination in Ovariectomized Guinea Pigs: Progesterone Deficiency and Decidual Collapse; J. Reprod. Fert. [1972]28:241–247).

In high dosages both antiestrogens and estrogens inhibit implantation in rats and mice (Martin, L.; Cox, R. J.; Emmens, C. W. [1963] Further Studies in the Effects of Estrogens and Antiestrogens on Early Pregnancy in Mice. J. Reprod. Fertil. 5:239–247; Singh, M. M.; Kamboj, V. P. [1992] Fetal Resorption in Rats Treated with an Antiestrogen in Relation to Luteal Phase Nidatory Estrogen Secretion. Acta endocrinol. 126:444–50). The implantation-inhibiting action of antiestrogens with estrogenic partial effects (nafoxidine, centchroman, tamoxifen) was also described in guinea pigs (Wisel, M. S.; Datta, J. K.; Saxena, R. N. [1994] Int. J. Fertil. 39:156–163). It is unclear whether the implantation-inhibiting action of the above-mentioned antiestrogens can be attributed to their antagonistic or agonistic action, since large-dose estrogens also prevent implantation in guinea pigs.

The use of estrogen antagonists (centchroman) for contraception in humans is also described (Nittyanand, S.; Kamboj, V. P. [1992] Centchroman: Contraceptive Efficacy and Safety Profile. International Conference on Fertility Regulation, Nov. 5–8, 1992 Bombay, India, Programme and Abstracts). In effective dosages, however, undesirable side effects occur that are attributable to the systemic effect of estrogen antagonists. Estrogen deprivation, which can occur after long-term treatment with an antiestrogen, at least limits its regular use for contraception.

Finally, the use of aromatase inhibitors for contraception in female primates of child-bearing age at a dosage at which the menstrual cycle of the female primate remains essentially unaffected is described in DE-A 42 13 005. Aromatase inhibitors block the biosynthesis of estrogens from their metabolic precursors. In this case the absolute level of the daily doses necessary for contraceptive action depends completely on the type of aromatase inhibitor used. For highly active aromatase inhibitors, the daily doses generally lie between about 0.05 and about 30 mg. In the case of less active aromatase inhibitors, the daily doses can also be higher.

An object of the invention is to provide a preparation for endometrial contraception (inhibition of endometrial receptivity, postcoital use, "pill on demand"), which does not have the above-mentioned undesirable side effects and at the same time exhibits greater contraceptive reliability than the separate administration of the corresponding individual components.

A "pill on demand" is defined as a pharmaceutical agent to be administered orally which, preferably with one-time and precoital use on demand, prevents conception. Such an agent, produced using exclusively a competitive progesterone antagonist, is described in unpublished German Patent Application P 44 38 820.9.

Upon further study of the specification and appended claims, further objects and advantages of this invention will become apparent to those skilled in the art.

These objects are achieved by using together at least one compound with a progesterone-antagonistic (PA) action and at least one compound with an antiestrogenic (AE) action, each in a non-ovulation-inhibiting dosage (e.g., in a single dosage unit), for the production of pharmaceutical agents for female contraception.

It has now been found that the combination of a progesterone antagonist and antiestrogen synergistically inhibits endometrium proliferation and differentiation, so that the antifertile effect of the individual components at the corresponding dosage in the combination is either enhanced or the individual components in the combination can be used at lower doses, to achieve a comparable effect when the individual components are used separately.

Agents that contain at least one compound with an antigestagenic action and at least one compound with an antiestrogenic action, especially for induction of labor and for abortion, as well as for treating gynecological disorders, as well as the use of at least one compound with an antigestagenic action and at least one compound with an antiestrogenic action for the production of pharmaceutical agents for the indications provided are objects of EP-A 0 310 541.

Pharmaceutical compositions for postcoital birth control that contain a competitive progesterone antagonist (antigestagen) as well as a progesterone and estrogen synthesis blocker, are described in U.S. Pat. No. 4,670,426. As a typical representative of the competitive progesterone antagonists to be used, fluocinolone acetonide, triamcinolone acetonide, steroids with a cyclic 16,17-acetal with acetone and 11β-[4-(dimethylamino)phenyl]-17β-hydroxy-17α-(1-propinyl)estra-4,9-dien-3-one (RU 38 486) and equivalent derivatives are mentioned. Here, the typical content lies between 20 and 50 mg. As examples of progesterone and estrogen synthesis blockers, aminoglutethimide, 4β,17α-dimethyl-17β-hydroxy-3-oxo-4α, 5-epoxy-5α-androstan-2α carbonitrile, 20,25-diazocholesterol and compounds with equivalent activity are cited, specifically at a dose of 300 to 1000 mg. According to U.S. Pat. No. 4,670,426, the application of the composition has to be done as early as possible within the first week after sexual intercourse over a period of 3 days; optimally, the treatment should be continued for 2 to 6 days. The prevention of nidation and thus of pregnancy is produced by synergistic effect when the two components of the composition are used together, with a success rate on the order of 90% or more.

It has now been found that in addition to antigestagens (competitive progesterone antagonists), pure estrogen antagonists, such as 7α-[9-[(4,4,5,5,5-pentafluorpentyl) sulfinyl]nonyl]estra-1,3,5(10)-trien-3,17β-diol (ICI 182780), or partial agonists such as tamoxifen, inhibit implantation in guinea pigs. This finding indicates that in guinea pigs, contrary to what was previously assumed, estrogens also play an important role in implantation.

In addition, it was found that in guinea pigs, surprisingly enough, combined treatment with progesterone antagonists and antiestrogens during the peri-implantation phase (day 1–7 post coitum) has a synergistic effect. These observations indicate that inguinea pigs, a conventional model for human contraception, the estrogens, perhaps formed in the blastocysts, play an important role during implantation.

The essential advantages of this invention certainly include the low dosage of the active ingredients, due on the one hand to the possible reduction of the effective amounts that are necessary in monotherapy owing to the synergistic effect, and on the other to the use of lower, non-ovulation-inhibiting dosages. Thus, the female menstrual cycle is in no way impaired in its cyclicity (as is caused by ovulation-inhibiting substances such as RU 486), and the organism is not burdened by unnecessarily large amounts of competitive progesterone antagonist or of antiestrogen. The use of such a progesterone antagonist/antiestrogen combination offers reliable contraception, i.e., the regular intake of such a medicine (daily, regularly every 3 to7 days) prevents nidation of the blastocysts without affecting the cycle. Further, the contraceptive reliability after one-time, demand-oriented precoital intake is increased regardless of the day of intake in the cycle ("pill on demand") or after postcoital treatment.

Because of the reduced dose of the antiestrogen, estrogen deprivation is not to be expected. An endometrium-selective action of the antiestrogen can be achieved and an unfavorable effect due to estrogen deprivation in other organs, for example, in bones, can be avoided.

In this connection, the ratio by weight of the two components in the new pharmaceutical agent can be varied within broad limits. Thus, both equal amounts of PA and AE and an excess of one of the two components can be used. The PA and AE are used together or separately, at a ratio by weight of essentially 50:1 to 1:50, preferably 25:1 to 1:25, and especially 10:1 to 1:10. If administered separately, simultaneous administration is preferred. Preferably, the PA and AE are administered combined in one dosage.

The two components can be administered once daily or intermittently every 3–6 days over the entire cycle. They can also be used on a one-time basis precoitally (as needed; "pill on demand") at any point in the menstrual cycle or postcoitally. In precoital use, the progesterone antagonist is preferably used at higher doses, but still below the ovulation-inhibiting dosage.

As competitive progesterone antagonists, all compounds are suitable that competitively block the action of progesterone on the gestagen receptor (progesterone receptor) and in this connection show no gestagenic activity of their own; the blocking can be produced by the substance administered itself or by its metabolites.

The competitive progesterone antagonists are preferably endometrium-specific (dissociated) compounds, according to this invention, which in most cases exhibit a weak antiovulatory activity. Non-dissociated progesterone antagonists can also be used, and then their dosage lies below the ovulation-inhibiting dose. For example, the following steroids are suitable:

11β-[4-(dimethylamino)phenyl]-17β-hydroxy-17α-(1-propinyl)estra-4,9-dien-3-one (RU-38 486),
11β-[4-(dimethylamino)phenyl]-17β-hydroxy-17α-(1-propinyl)-18α-homoestra-4,9-dien-3-one and
11β-[4-(dimethylamino)phenyl]-17aβ-hydroxy-17aα-(1-propinyl) -17a-homoestra-4,9,16-trien-3-one(all EP-A-0 057 115),
in addition
17α-ethinyl-17β-hydroxy-11β-(4-methoxyphenyl) estra-4,9-dien-3-one (Steroids 37 (1981), 361–382),
11β-(4-acetylphenyl)-17β-hydroxy-17α-(1-propinyl)estra-4,9-dien-3-one (EP-A 0 190 759), 4',5'-dihydro-11β-[4-(dimethylamino)phenyl]-6β-methyl-spiro[estra-4,9-dien-17β2'(3'H)-furan]-3-one
11β-(4-acetylphenyl)-19,24-dinor-17,23-epoxy-17α-chola-4,9,20-trien-3-one,
4',5'-dihydro-11β-[4-(dimethylamino)phenyl]-7β-methyl-spiro[estra-4,9-dien-17β, 2'(3'H)-furan]-3-one U.S. Pat No. 4,386,085)
as well as the 11β-aryl-14β-estradienes and -trienes described in EP-A 0 277 676, the 19,11β-bridged steroids, which are the object of EP-A-0 283 428, the 11β-aryl-6-alkyl (or 6-alkenyl or 6-alkinyl)-estradienes and -pregnadienes known from EP-A-0 289 073 and the 11β-aryl-7-methyl (or 7-ethyl)-estradienes known from EP-A-0 321 010, as well as the 10β-H steroids of EP-A-0 404 283, for example, (Z)-11β-[4-(dimethylamino)phenyl]-17α-(3-hydroxy-1-propenyl)estr-4-en-17β-ol.

In addition, the following can be mentioned as typical representatives of competitive progesterone antagonists that can be used in accordance with the invention, for example:
11β-[4-(dimethylamino)phenyl]-17α-hydroxy-17β-(3-hydroxypropyl)-13α-estra-4,9-dien-3one (Onapristone) (EP-A 0 129 499);
(Z)-11β-(4-acetylphenyl)-17β-hydroxy-17α-(3-hydroxy-1-propenyl)estra-4,9-dien-3-one (EP-A 0 190 759);
(Z)-6'-(4-cyanophenyl-9,11α-dihydro-17β-hydroxy-17o(3-hydroxy-17α(3-hydroxy-1-propenyl)-4'H-naphth[3',2', 1':10,9,11]estra4,9(11)-dien-3-one and
(Z)-9,11α-dihydro-17β-hydroxy-17α-(3-hydroxy-1-propenyl)-6'-(3-pyridinyl)-4'H-naphth[3',2',1':10,9, 11]estra-4, 9(11)-dien-3-one (both EP-A-O 283 428);
17α-hydroxy-17β-(3-hydroxypropyl)-11β-[4-(1-methylethenyl)phenyl]-13α-estra-4,9-dien 3-one (ZK 131 535) and
11β-[4-(3-furanyl)phenyl]-17α-hydroxy-17β-(3-hydroxypropyl)-13α-estra-4,9-dien-3one (ZK 135 695) (both EP-A 0 349 481);
(Z) -11β-[4-(dimethylamino)phenyl]-17β-hydroxy-17α-(3-hydroxy-1-propenyl)estr-4-en-3-one (EP-A 0 404 283);
(E)-11β-[4-[[(acetyloxy)imino]methyl]phenyl]-17β-methoxy-17β-(methoxymethyl)estra-4,9-dien-3-one (EP-A 0 648 778, EP-A 0 648 779);
(E)-11-β-[4-[[[(ethoxycarbonyl)oxy]imino]methyl]phenyl]-17β-methoxy-17α-(methoxymethyl)estra-4,9-dien-3-one (EP-A 0 648 778, EP-A 0 648 779);

The last-mentioned PAs are of dissociated type, in which changes in the endometrium are observed at a certain threshold dose, while ovulation (central effect) is not inhibited. The ratio of ovulation-inhibiting to abortive dose (dissociation factor) can be used as a yardstick for dissociation. Dissociated PAs are preferred within the scope of this invention.

The above list of PAs is not exhaustive. Other competitive progesterone antagonists described in the above-mentioned publications, as well as those from publications not mentioned here, are also suitable. Recently, non-steroidal compounds that act as antagonists on the progesterone receptor have also become known (WO-A 93/21145), which can be used for the purpose of this invention.

The competitive progesterone antagonists can be administered, for example, locally, topically, enterally, transdermally or parenterally. For the preferred oral administration, especially tablets, coated tablets, capsules, pills, suspensions, or solutions that can be produced in the usual way with the additives and vehicles commonly used in galenicals are suitable. For local or topical use, for example, vaginal suppositories, vaginal gels, implants, vaginal rings, intrauterine release systems (IUDs) or transdermal systems such as skin patches are suitable.

A dosage unit contains a non-ovulation inhibiting amount of preferably 0.25–50 mg of 11β-[4-(dimethylamino) phenyl]-17α-hydroxy-17β-(3-hydroxypropyl) -13α-estra-4, 9-dien-3-one (Onapristone) or a biologically equivalent non-ovulation inhibiting amount of another competitive progesterone antagonist.

Effective biologically equivalent amounts can be determined in a nidation inhibition test on guinea pigs (treatment day 1–7 post coitum). See, e.g., Tests 1–3 described below.

If the administration of the pharmaceutical agent produced according to the invention is done by an implant, a vaginal ring, an IUD or a transdermal system, these administration systems must be designed in such a way that the dose of the competitive progesterone antagonist that is released daily lies in this range of non-ovulation inhibiting amounts, preferably about 0.25–50 mg.

The dose of a competitive progesterone antagonist to be administered according to the invention can lie in the both non-ovulation-inhibiting dose range and the non-abortion-triggering dose range of the progesterone antagonist in question.

As compounds having an antiestrogenic action, estrogen antagonists (competitive antiestrogens) are primarily suitable according to the invention. Estrogen antagonists according to this invention can be derived both from steroids or nonsteroidal compounds. Estrogen antagonists according to this invention are to be understood to mean only those compounds that act as selectively as possible, i.e., ones which essentially inhibit only the action of estrogens and/or reduce their concentration.

Estrogen antagonists act by displacing estrogen from the receptor.

As estrogen antagonists, all commonly used compounds with competitive antiestrogenic action at the receptor are suitable. They can be used in bioequivalent amounts of estrogen antagonists that are already commercially available, i.e., the daily dose is preferably about 5–100 mg. for tamoxifen or a biologically equivalent amount of another estrogen antagonist.

As nonsteroidal estrogen antagonists, for example, the following can be mentioned:

| Tamoxifen | (Z)-N,N-dimethyl-2-[4-(1,2-diphenyl-1-butenyl)phenoxy]ethanamine |
| --- | --- |
| Nafoxidine | 1-[2-[4-(3,4-dihydro-6-methoxy-2-phenyl-1-naphthalinyl)phenoxy]ethyl]-pyrrolidine hydrochloride |
| Mer 25 | α-[4-[2-(diethylamino)ethoxy]phenyl]-4-methoxy-α-phenylbenzene-ethanol |
| Raloxifen | [6-hydroxy-2-(4-hydroxyphenyl)-3-benzothienyl][4-[2-(1-piperidinyl)-hydrochloride |
| Centchroman | (3R-trans)-3,4-dihydro-2,2,-dimethyl -7-methoxy-3-phenyl-4-[4-[2-(1-pyrrolidinyl)ethoxy]phenyl]-2H-1-benzopyran | other compounds of 1,1,2-triphenylbut-1-ene type, especially 3,3'-(2-phenyl-1-buten-1-ylidene)bis[phenol]-diacetate [J. Cancer Res. Clin. Oncol., (1986), 112, pp. 119–124].

In addition, the following are suitable as steroidal estrogen antagonists, for example:
17α-ethinyl-11α-methylestra-1,3,5(10)-trien-3,17β-diol and 16β-ethylestra-1,3,5(10)-trien-3,17β-diol,
N-butyl-11-,(3,17β-dihydroxyestra-1,3,5(10)-trien-7α-yl)-N-methylundecane acid amide and
7α-[9-[(4,4,5,5,5-pentafluorpentyl)sulfinyl]nonyl]-estra-1, 3,5(10)-trien-3,17β-diol.

According to the invention, in any case estrogen antagonists that have an especially strong and as selective as possible an effect on the endometrium are preferred (for instance, Tamoxifen, Nafoxidin, 7α-[9-[(4,4,5,5, 5pentafluorpentyl)sulfinyl]nonyl]estra-1,3,5(10)-trien3, 17β-diol).

The threshold dose for an endometrium-selective action is determined on ovariectomized, estradiol-substituted rats. The parameter used is mytotic activity (proliferation marker: PCNA). The threshold dose is the amount of estrogen antagonist at which only one effect is observed on the uterus, namely an inhibition of estrogen-induced proliferation of the endometrium.

As antiestrogens according to this invention, aromatase inhibitors can also be used in connection with progesterone antagonists. Aromatase inhibitors suppress the synthesis of estrogens from their precursors. Examples of aromatase inhibitors are atamestane=1-methylandrosta-1,4-dien-3,17-dione (DE-A 33 22 285), pentrozol=5-[cyclopentyliden(1H-imidazol-1-yl)methyl]-2-thiopencarbonitrile (EP-A 0 411 735) or 4-(5,6,7,8-tetrahydroimidazo-[1,5-a]pyridin-5-yl) benzonitrile monohydrochloride (Cancer Res., 48, pp. 834–838, 1988).

The use of estrogen antagonists, however, is preferred over that of aromatase inhibitors, since the estrogen antagonists do not affect the serum-estrogen concentration and thus impairment of the cycle is avoided.

An AE dosage unit contains a non-ovulation inhibiting amount of preferably about 0.01–100 mg of tamoxifen or a biologically equivalent non-ovulation inhibiting amount of another antiestrogenically effective compound. Its formulation can be done analogously to that of the progesterone antagonists.

Biologically equivalent amounts of other antiestrogenic compounds can be determined by performing nidation inhibition tests on guinea pigs. See, e.g., Tests 1–3 described below.

Compounds with progesterone-antagonistic action and compounds with antiestrogenic action can be administered, e.g., locally, topically, enterally, or parenterally.

The progesterone antagonist and the antiestrogen preferably are used in a combined dosage unit.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding German application P 44 47 402.4, filed Dec. 23, 1994, are hereby incorporated by reference.

BRIEF DESCRIPTION OF THE DRAWINGS

Various other features and attendant advantages of the present invention will be more fully appreciated as the same becomes better understood when considered in conjunction with the accompanying drawings, in which like reference characters designate the same or similar parts throughout the several views, and wherein.

Figure 1:
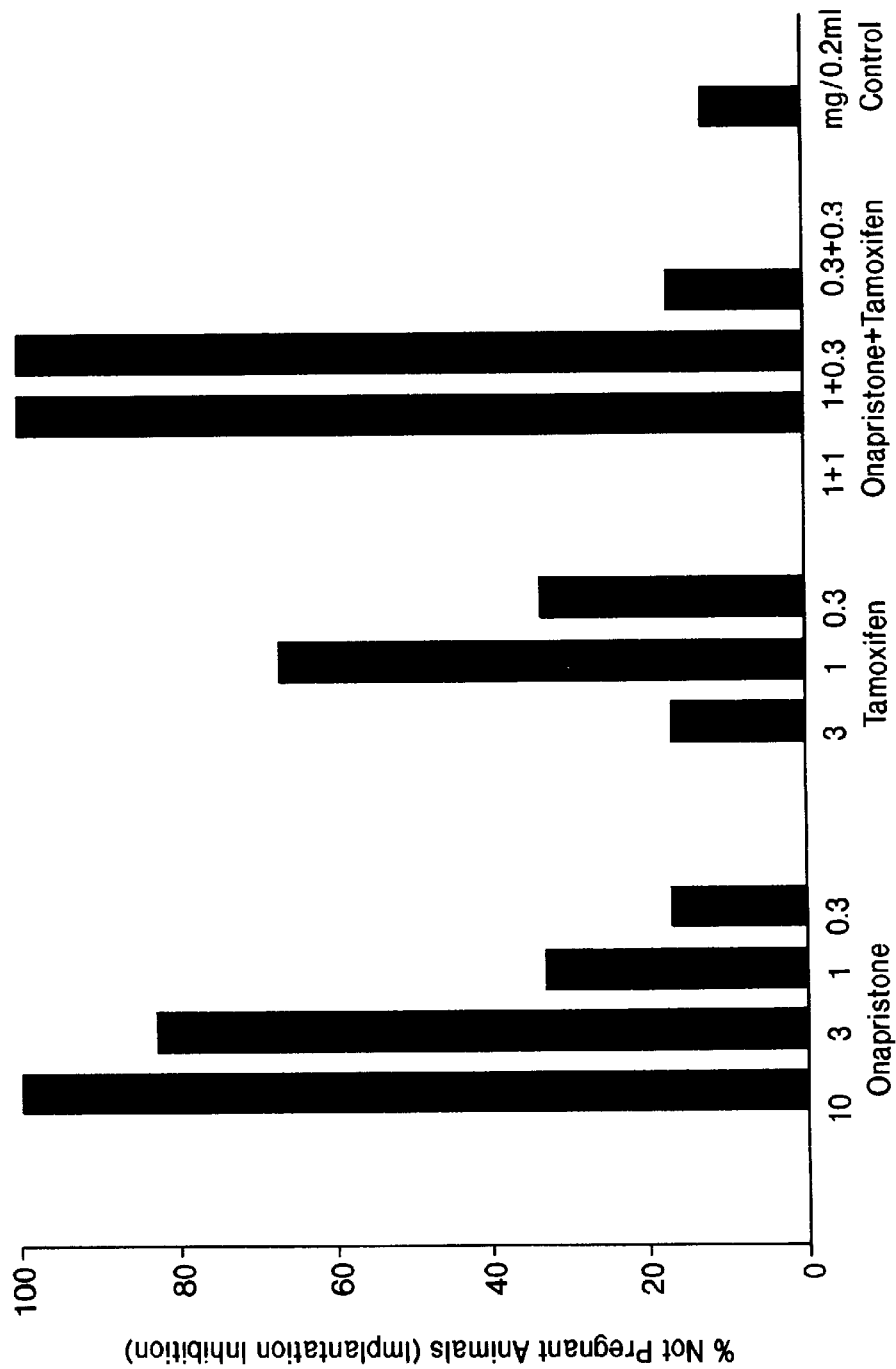
FIG. 1 is a bar graph illustrating the implantation inhibition activity of onapristone alone, tamoxifen alone, and the combination of onapristone and tamoxifen.

The examples below are used for a more detailed explanation of this invention.

EXAMPLES

Example 1

10.0 mg of 11β-[4-(dimethylamino)phenyl]-17α-hydroxy-17β-(3-hydroxypropyl)-13α-estra-4,9dien-3-one
140.5 mg of lactose
69.5 mg of corn starch
2.5 mg of polyvinylpyrrolidone
2.0 mg of aerosil
0.5 mq of magnesium stearate
225.0 mg total weight of the tablet

Example 2

20.0 mg of tamoxifen (antiestrogen with agonistic partial action)
50.0 mg of 11β-[4-(dimethylamino)phenyl]-17α-hydroxy-17β-(3-hydroxypropyl)-13α-estra-4,9dien-3-one
105.0 mg of lactose
40.0 mg of corn starch
2.5 mg of poly-N-vinylpyrrolidone 25
2.0 mg of aerosil
0.5 mg of magnesium stearate
220.0 mg total weight of the tablet. The tablet is produced in the usual way in a tablet press. Optionally, the active ingredients according to the invention can also be pressed separately into a two-layer tablet with respectively half of the above-indicated additives.

Example 3

5.0 mg of 7α-[9-[(4,4,5,5,5-pentafluorpentyl)sulfinyl]-nonyl]estra-1,3,5(10)-trien-3,17β-diol (pure antiestrogen)
50.0 mg of 11β-[4-(dimethylamino)phenyl]-17α-hydroxy-17β-(3-hydroxypropyl)-13α-estra-4,9-dien-3-one
110.0 mg of lactose
50.0 mg of corn starch
2.5 mg of poly-N-vinylpyrrolidone 25
2.0 mg of aerosil
0.5 mg of magnesium stearate
220.0 mg total weight of the tablet. The tablet is produced in the usual way in a tablet press. Optionally, the active ingredients according to the invention can also be pressed separately into a two-layer tablet with respectively half of the above-indicated additives.

Example 4

0.5 mg of 11β-[4-(dimethylamino)phenyl]-17α-hydroxy-17β-(3-hydroxypropyl)-13α-estra-4,9-dien-3-one
0.2 mg of 7α-[9-[(4,4,5,5,5-pentafluorpentyl)sulfinyl]-nonyl]estra-1,3,5(10)-trien-3,17β-diol (pure antiestrogen)
159.5 mg of lactose
54.8 mg of corn starch
2.5 mg of poly-N-vinylpyrrolidone 25
2.0 mg of aerosil
0.5 mg of magnesium stearate
220.0 mg total weight of the tablet. The tablet is produced in the usual way in a tablet press. Optionally, the active ingredients according to the invention can also be pressed separately into a two-layer tablet with respectively half of the above-indicated additives.

Example 5

Composition of an Oily Solution
100.0 mg of tamoxifen
343.4 mg of castor oil
608.6 mg of benzyl benzoate
1052.0 mg=1 ml
The solution is loaded into an ampoule.

Example 6

5.0 mg of 11β-[4-dimethylamino)phenyl]-17β-hydroxy-17α (1-propinyl)estra-4,9-dien-3-one (RU-38486),
10.0 mg of (Z)-N,N-dimethyl-2-[(4-(1,2-diphenyl-1-butenyl)phenoxy]ethanamine (Tamoxifen; antiestrogen with an agonistic partial action)
140.0 mg of lactose
60.5 mg of corn starch
2.5 mg of poly-N-vinylpyrrolidone 25
2.0 mq of aerosil
220.0 mg total weight of the tablet. The tablet is produced in the usual way in a tablet press. Optionally, the active ingredients according to the invention can also be pressed separately into a two-layer tablet with respectively half of the above-indicated additives.

Pharmacological Observations

Test 1

The tests were carried out on normal guinea pigs with a normal cycle. The treatment was begun on day 1 post coitum. The animals were treated over 6 days with a vehicle (benzyl benzoate/castor oil), or Tamoxifen ((Z) -N,N-dimethyl-2-[4-(1,2-diphenyl-1-butenyl)phenoxy] ethanamine) at a dose of 0.3, 1, 3 mg/day/animal or the progesterone-antagonistic-action compound onapristone 11β-[4-(dimethylamino)phenyl]-17α-hydroxy-17β-(3-hydroxypropyl) -13α-aestra-4,9-dien-3-one (0.3, 1.0 or 3 mg/day/animal), in each case alone or with a combination of the two compounds. The substances were administered subcutaneously. The parameter used is the number of implantation points on is day 12 post coitum.

The combination of threshold doses of the two components (AG 0.3, 1 mg/AE about 0.3, 1 mg) results in a significant increase in effectiveness (100% implantation inhibition in the case of 1 mg of AG+1 mg of AE and 1 mg of AG+0.3 mg of AE) after a six-day treatment (FIG. 1). The synergistic effect of both components is more strongly pronounced after an 8-day treatment.

Test 2

The tests were carried out on normal guinea pigs with a normal cycle. The treatment was begun on day 1 p.c. The animals (n=6/group) were treated over 6 days with a vehicle (benzyl benzoate/castor oil) or Tamoxifen at a dose of 0.3, 1, 3 mg/kg/animal or the progesterone-antagonistic-action effective compound (Z)-11β-[4-(dimethylamino)phenyl]-17α-(3-hydroxy-1-propenyl)estr-4-en-17β-ol in each case alone or with a combination of both compounds. The substances were administered s.c. The parameter used is the number of nonpregnant animals on day 12.

Figure 2:
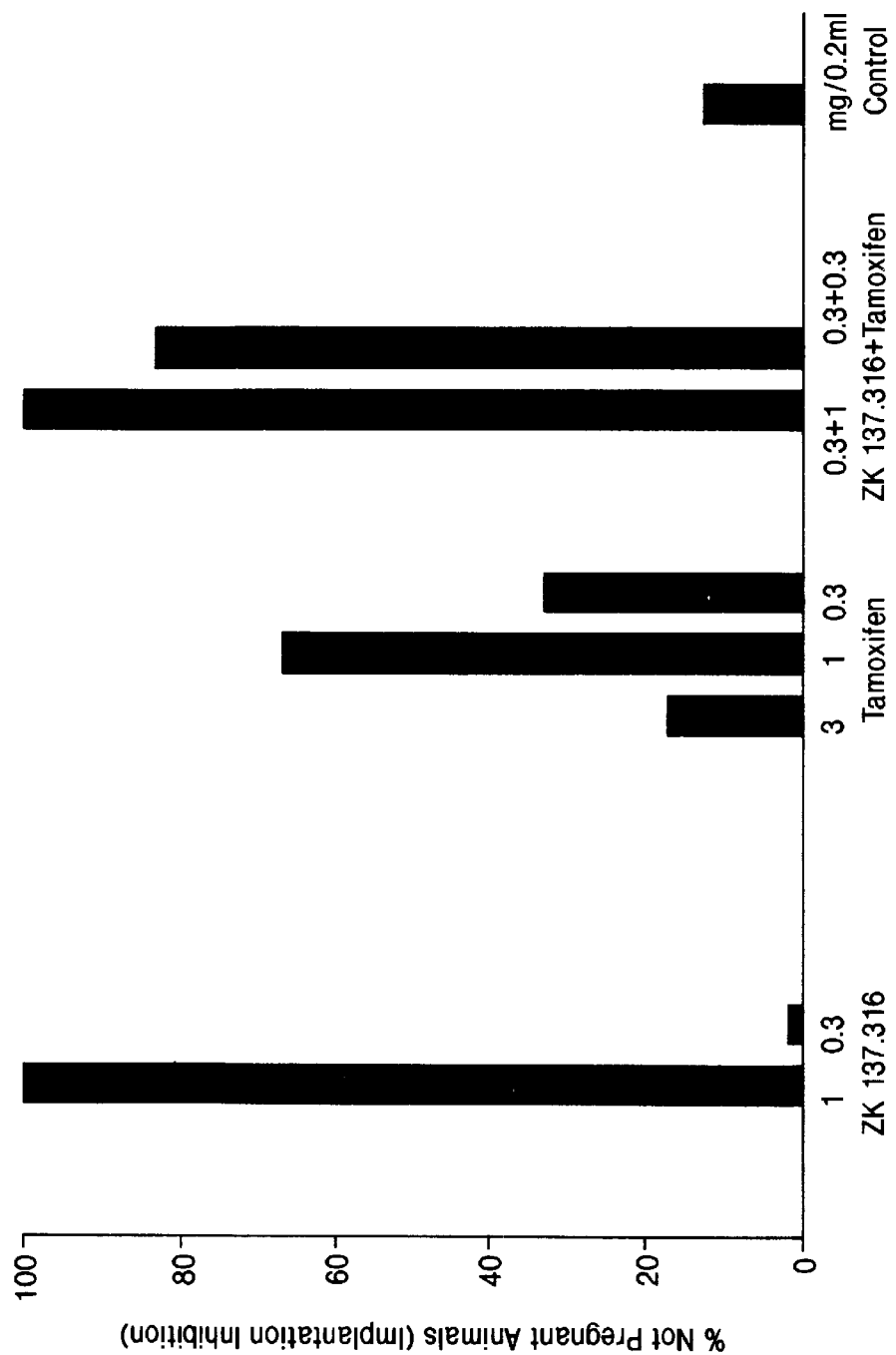
FIG. 2 is a bar graph illustrating the implantation inhibition activity of (Z)-11β-[4-(dimethyl-amino)phenyl]-17α-(3-hydroxy-1propenyl)estr-4-en-17β-ol alone, tamoxifen alone, and the combination thereof.

The combination of threshold doses (0.3 mg of (Z)-11β-[4-(dimethylamino)phenyl]-17α-(3-hydroxy-1-propenyl) estra-4-en-17β-ol+0.3 mg of AE) results in a significant increase in effectiveness (about 80% receptivity inhibition, FIG. 2).

Test 3

The tests were carried out on normal guinea pigs with a normal cycle over a treatment period of 2 cycles. Mating took place in the second cycle.

Doses of Onapristone: 0.1, 0.25, 0.5, 1.0 and 3.0 mg daily s.c.

Doses of Tamoxifen: 0.1, 0.25, 0.5, 1.0, 3.0 and 10.0 mg daily s.c.

The combination of single doses that are only marginally effective separately (onapristone 0.5 mg; tamoxifen 0.5 mg) results in a pronounced enhancement of action (synergism). Only when using a combination as defined by this invention can a complete avoidance of pregnancy be achieved. In the above-mentioned dosage range of tamoxifen (0.1–10.0 mg/animal), no complete inhibition of receptivity could be achieved. Normal pregnancies were observed at 30% (10.0 mg) and 90% to 100% (<1.0 mg) Also, after treatment with high onapristone doses, occasional pregnancies occurred.

After a combination treatment with onapristone and tamoxifen (1.0 mg in each case), a complete inhibition of receptivity was observed in all cases. 100% receptivity inhibition means complete avoidance of pregnancies.

At lower doses of tamoxifen and onapristone (<1.0 mg), which by themselves have no effect or a marginal effect, the receptivity-inhibition rate was approximately 80% to 100% of all animals.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of effecting contraception comprising preventing nidation of a fertilized egg in a female mammal by administering a non-ovulation-inhibiting amount of at least one compound with competitive progesterone-antagonistic activity and a non-ovulation-inhibiting amount of at least one competitive estrogen antagonist.

2. A method according to claim 1, wherein postcoital birth control is effected by administering said compounds postcoitally on a one-time basis.

3. A method according to claim 1, wherein demand-oriented birth control is effected by administering said compounds on a one-time basis at any point in the menstrual cycle.

4. A method according to claim 1, wherein said at least one compound with progesterone antagonistic activity is:
11β-[4-(dimethylamino)phenyl]-17α-hydroxy-17β-(3-hydroxypropyl)-13a-estra-4,9-dien-3-one;
(Z)-11β-(4-acetylphenyl)-17β-hydroxy-17α-(3-hydroxy-1-propenyl)estra-4,9-dien-3-one;
(Z)-6'-(4-cyanophenyl-9,11α-dihydro-17β-hydroxy-17α-(3-hydroxy-1-propenyl)-4'H-naphth[3',2',1',:10,9,11]estra-4,9(11)-dien-3-one;
(Z)-9,11α-dihydro-17β-hydroxy-17α-(3-hydroxy-1-propenyl)-6'-(3-pyridinyl)-4'H-naphth [3',2',1':10,9,11]estra-4,9(11)-dien-3one;
17α-hydroxy-17β-(3-hydroxypropyl)-11β-[4-(1-methylethenyl)phenyl]-13α-estra-4,9-dien-3-one;
11β-[4-(3-furanyl)phenyl]-17α-hydroxy-17β-(3-hydroxypropyl)-13α-estra-4,9-dien-3-one;
(Z)-11β-[4-(dimethylamino)phenyl]-17β-hydroxy-17α-(3hydroxy-1-propenyl)estr-4-en-3-one;
(E)-11β-[4-[[(acetyloxy)imino]methyl]phenyl]-17β-methoxy-17α-(methoxymethyl)estra-4,9-dien-3-one; or
(E)-11β-[4-[[[(ethoxycarbonyl)oxy]imino]methyl]phenyl]-17β-methoxy-17α-(methoxymethyl)estra-4,9-dien-3-one.

5. A method according to claim 1, wherein said estrogen antagonist is:
(Z)-N,N-dimethyl-2-[4-(1,2-diphenyl-1-butenyl)phenoxy]ethanamine;
1-[2-[4-(3,4-dihydro-6-methoxy-2-phenyl-1-naphthalinyl)phenoxy]ethyl]pyrrolidine hydrochloride;
[6-hydroxy-2-(4-hydroxyphenyl)-3-benzothienyl][4-[2-(1-piperidinyl)ethoxy]phenyl]methanone hydrochloride;
N-butyl-11-(3,17β-dihydroxyestra-1,3,5(10)-trien-7α-yl)-N-methylundecane acid amide; or
7α-[9-[(4,4,5,5,5-pentafluorpentyl)sulfinyl]nonyl]estra-1,3,5(10)-trien-3,17β-diol.

6. A method according to claim 1, wherein said compound with progesterone antagonistic activity is (Z)-11β-[4-(dimethylamino)phenyl]-17α-(3-hydroxy-1-propenyl)estr-4-en-17β-ol and said estrogen antagonist is (Z)-N,N-dimethyl-2-[4-(1,2-diphenyl-1-butenyl)phenoxy]ethanamine.

7. A method according to claim 1, wherein said compounds are administered locally or topically.

8. A method according to claim 1, wherein said compounds are administered enterally or parenterally.

9. A method according to claim 1, wherein said compound with progesterone antagonistic activity and said estrogen antagonist are administered together.

10. A method according to claim 1, wherein said compound with progesterone antagonistic activity and said estrogen antagonist are administered separately.

11. A method according to claim 9, wherein said compound with progesterone antagonistic activity and said estrogen antagonist are administered simultaneously.

12. A method according to claim 2, wherein said at least one compound with progesterone antagonistic activity is:
11β-[4-(dimethylamino)phenyl]-17α-hydroxy-17β-(3-hydroxypropyl)-13α-estra-4,9-dien-3-one;
(Z)-11β-(4-acetylphenyl)-17β-hydroxy-17α-(3-hydroxy-1propenyl)estra-4,9-dien-3-one;
(Z)-6'-(4-cyanophenyl-9,11α-dihydro-17β-hydroxy-17α-(3-hydroxy-1-propenyl)-4'H-naphth[3',2',1':10,9,11]estra-4,9(11)-dien-3-one;
(Z)-9,11α-dihydro-17β-hydroxy-17α-(3-hydroxy-1-propenyl)-6'-(3-pyridinyl)-4'H-naphth[3',2',1':10,9,11]estra-4,9(11)-dien-3-one;
17α-hydroxy-17β-(3-hydroxypropyl)-11β-[4-(1-methylethenyl)phenyl]-13α-estra-4,9-dien-3-one;
11β-[4-(3-furanyl)phenyl]17α-hydroxy-17β-(3-hydroxypropyl)-13α-estra-4,9-dien-3-one;
(Z)-11β-[4-(dimethylamino)phenyl]-17β-hydroxy-17α-(3-hydroxy-1-propenyl)estr-4-en-3-one;
(E)-11β-[4-[[(acetyloxy)imino]methyl]phenyl]-17β-methoxy-17α-(methoxymethyl)estra-4,9-dien-3-one; or
(E)-11β-[4-[[[(ethoxycarbonyl)oxy]imino]methyl]phenyl]-17β-methoxy-17α-(methoxymethyl)estra-4,9-dien-3-one.

13. A method according to claim 3, wherein said at least one compound with progesterone antagonistic activity is:
11β-[4-(dimethylamino)phenyl]-17α-hydroxy-17β-(3-hydroxypropyl)-13α-estra-4,9-dien-3-one;
(Z)-11β-(4-acetylphenyl)-17β-hydroxy-17α-(3-hydroxy-1-propenyl)estra-4,9-dien-3-one;
(Z)-6'-(4-cyanophenyl-9,11α-dihydro-17β-hydroxy-17α-(3-hydroxy-1-propenyl)-4'H-naphth[3',2',1':10,9,11]estra-4,9(11)-dien-3-one;
(Z)-9,11α-dihydro-17β-hydroxy-17α-(3-hydroxy-1-propenyl)-6'-(3-pyridinyl)-4'H-naphth[3',2',1':10,9,11]estra-4,9(11)-dien-3-one;
17α-hydroxy-17β-(3-hydroxypropyl)-11β-[4-(1-methylethenyl)phenyl]-13α-estra-4,9-dien-3-one;
11β-[4-(3-furanyl)phenyl]-17α-hydroxy-17β-(3-hydroxypropyl)-13αestra-4,9-dien-3-one;

(Z)-11β-[4-(dimethylamino)phenyl]-17β-hydroxy-17α-(3-hydroxy-1-propenyl)ester-4en-3-one;

(E)-11β-[4-[[(acetyloxy)imino]methyl]phenyl]-17β-methoxy-17α-(methoxymethyl)estra-4,9-dien-3-one; or (E)-11β-[4-[[[(ethoxycarbonyl)oxy]imino]methyl]phenyl]-17β-methoxy-17α-(methoxymethyl)estra-4,9-dien-3-one.

14. A method according to claim 4, wherein said estrogen antagonist is:

(Z)-N,N-dimethyl-2-[4-(1,2-diphenyl-1-butenyl)phenoxy]ethanamine;

1-[2-[4-(3,4-dihydro-6-methoxy-2-phenyl-1-naphthalinyl)phenoxy]ethyl]pyrrolidine hydrochloride;

[6-hydroxy-2-(4-hydroxyphenyl)-3-benzothienyl][4-[2-(1-piperidinyl)ethoxy]phenyl]methanone hydrochloride;

N-butyl-11-(3,17β-dihydroxyestra-1,3,5(10)-trien-7α-yl)-N-methylundecane acid amide; or 7α-[9-[(4,4,5,5,5-pentafluorpentyl)sulfinyl]nonyl]estra-1,3,5(10)-trien-3,17β-diol.

15. A method according to claim 1, wherein said compounds are administered precoital.

16. A method according to claim 1, wherein said female mammal is a human.

17. A method according to claim 1, wherein said compound with progestogen antagonistic activity and said estrogen antagonist are administered in a weight ratio of 50:1 to 1:50.

18. A method according to claim 1, wherein said compounds are administered daily every 3–7 days.

19. A method according to claim 1, wherein said compounds are administered in a combined dosage unit.

20. A method according to claim 1, wherein said compounds are administered daily every 3–6 days over the entire menstrual cycle.

21. A method according to claim 1, wherein said compound with progesterone-antagonistic activity is of the dissociated type and said estrogen antagonist is of the non-dissociated type.

22. A method according to claim 1, wherein said at least one compound with progesterone-antagonistic activity is (Z)-11β-[4-(dimethylamino)phenyl]-17β-hydroxy-17α-(3-hydroxy-1-propenyl)estr-4-en-3-one, and said at least one estrogen antagonist is 7α-[9-[(4,4,5,5,5,-pentafluorpentyl)sulfinyl]nonyl]-estra-1,3,5,(10)-trien-3,17β-diol.

23. A method of effecting contraception by inhibition of endometrial receptivity in a female mammal comprising administering a non-ovulation-inhibiting amount of at least one compound with progesterone-antagonistic activity and a non-ovulation-inhibiting amount of at least one estrogen antagonist.

24. A method according to claim 1, wherein ovulation is not disrupted.

25. A method according to claim 1, wherein the menstrual cycle is not disrupted.

26. A method according to claim 23, wherein ovulation is not disrupted.

27. A method according to claim 23, wherein the menstrual cycle is not disrupted.

28. A method according to claim 1, wherein said compound with progestogen antagonistic activity and said estrogen antagonist are administered in a weight ratio of 25:1 to 1:25.

29. A method according to claim 1, wherein said compound with progestogen antagonistic activity and said estrogen antagonist are administered in a weight ratio of 10:1 to 1:10.

30. A method according to claim 15, wherein said compounds are administrated on a one-time basis.

31. A method according to claim 1, wherein the compound with progesterone-antagonistic activity is (Z)-11β-[4-(dimethylamino)phenyl]-17β-hydroxy-17α-(3-hydroxy-1-propenyl)estr-4-en-3-one and the estrogen antagonist is 7α-[9-[(4,4,5,5,5-pentafluorpentyl)sulfinyl]nonyl]estra-1,3,5,(10)-trien-3,17β-diol).

32. A method according to claim 1, wherein the compound with progesterone-antagonistic activity is (Z)-11β-[4-(dimethylamino)phenyl]-17β-hydroxy-17α-(3-hydroxy-1propenyl)estr-4-en-3-one and the estrogen antagonist is Tamoxifen.

33. A method according to claim 1, wherein the compound with progesterone-antagonistic activity is Onapristone and the estrogen antagonist is 7α-[9-[(4,4,5,5,5-pentafluorpentyl)sulfinyl]nonyl]estra-1,3,5(10)-trien-3,17β-diol.

34. A method according to claim 1, wherein the compound with progesterone-antagonistic activity is Onapristone and the estrogen antagonist is Tamoxifen.

* * * * *

UNITED STATES PATENT AND TRADEMARK OFFICE
CERTIFICATE OF CORRECTION

PATENT NO. : 6,362,237 B1
DATED : March 26, 2002
INVENTOR(S) : Kristof Chwalisz et al.

It is certified that error appears in the above-identified patent and that said Letters Patent is hereby corrected as shown below:

Column 11,
Line 46, reads "13a-estra" should read -- 13α-estra --
Line 54, reads "dien-eone;" should read -- dien-3-one; --
Line 60, reads "(3hydroxy)" should read -- (3-hydroxy) --

Column 12,
Line 34, reads "1propenyl)" should read -- 1-propenyl) --
Line 67, reads "13αestra" should read -- 13α-estra --

Column 13,
Line 2, reads "ester-4en" should read -- estr-4-en --
Line 43, reads "4,4,5,5,5,-pentafluorpentyl)" should read
-- 4,4,5,5,5-pentafluorpentyl) --

Column 14,
Line 33, reads "1propenyl)" should read -- 1-propenyl) --

Signed and Sealed this

Twenty-second Day of March, 2005

JON W. DUDAS
*Director of the United States Patent and Trademark Office*